(12) United States Patent
Chen et al.

(10) Patent No.: US 7,066,927 B2
(45) Date of Patent: Jun. 27, 2006

(54) VENTED SEAL HAVING REDUNDANT SEALING COMPONENTS

(75) Inventors: David E. Chen, Fremont, CA (US); Erik W. Peterson, Walnut Creek, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 146 days.

(21) Appl. No.: 10/758,400

(22) Filed: Jan. 15, 2004

(65) Prior Publication Data

US 2005/0156387 A1    Jul. 21, 2005

(51) Int. Cl.
*A61B 17/00* (2006.01)
*F16J 15/32* (2006.01)

(52) U.S. Cl. .......................... 606/1; 277/563; 277/585; 277/552; 137/625.69

(58) Field of Classification Search ................ 277/563, 277/585, 552, 502, 607, 615; 137/625.69, 137/625.66
See application file for complete search history.

(56) References Cited

U.S. PATENT DOCUMENTS

| | | | | |
|---|---|---|---|---|
| 2,612,393 A * | 9/1952 | Dahlgren | ............... | 277/585 |
| 2,754,136 A * | 7/1956 | Phillips | ............... | 277/322 |
| 2,983,533 A * | 5/1961 | Tisch | ............... | 277/649 |
| 2,988,148 A * | 6/1961 | Conrad et al. | ............... | 277/337 |
| 3,175,833 A * | 3/1965 | Morse | ............... | 277/574 |
| 3,190,661 A | 6/1965 | Wahl et al. | | |
| 3,414,273 A * | 12/1968 | Sumner | ............... | 277/626 |
| 3,510,177 A | 5/1970 | Shimula | | |
| 3,568,436 A | 3/1971 | Heffner et al. | | |
| 3,829,104 A | 8/1974 | Green | | |
| 3,854,737 A * | 12/1974 | Gilliam, Sr. | ............... | 277/566 |
| 4,146,237 A | 3/1979 | Bergman | | |
| 4,222,575 A | 9/1980 | Sekiguchi et al. | | |
| 4,303,250 A * | 12/1981 | Persson | ............... | 277/585 |
| 4,413,829 A | 11/1983 | Pietsch | | |
| 4,491,155 A * | 1/1985 | Meyer et al. | ............... | 137/625.66 |
| 4,572,515 A * | 2/1986 | Grazioli | ............... | 277/649 |
| 4,693,343 A | 9/1987 | Boyd | | |
| 4,756,536 A | 7/1988 | Belcher | | |
| 4,809,989 A * | 3/1989 | Kernal | ............... | 277/337 |
| 5,009,435 A | 4/1991 | Villanyi et al. | | |
| 5,037,431 A * | 8/1991 | Summers et al. | ............... | 606/131 |
| 5,190,078 A * | 3/1993 | Stoll et al. | ............... | 137/625.69 |

(Continued)

OTHER PUBLICATIONS

The QUAD Seal Family—Custom-Molded Products: Minnesota Rubber and QMR Plastics Quadion Corporation; pp. 1-2; Oct. 6, 2003; http://www.mnrubber.com/factbook/4-9.htm.

*Primary Examiner*—Alison K. Pickard
(74) *Attorney, Agent, or Firm*—Michael Best & Friedrich LLP

(57) ABSTRACT

A seal having a body and several bands extending away from the body. The bands extend around an axial portion of the body. In some embodiments, the bands project from and are formed integral with the body. For example, the bands can be rings. Two bands can be located on the outside of the body and two additional bands can be located on the inside of the body to provide redundant sealing components between separated fluids. A vent aperture can be positioned between the two bands on each side of the body. The two inner bands can be offset from the two outer bands. The seal can be used in a surgical cutting device, among other things.

14 Claims, 2 Drawing Sheets

U.S. PATENT DOCUMENTS 5,584,488 A * 12/1996 Lembcke .................... 277/314
5,591,184 A *  1/1997 McDonnell et al. ........ 606/167
5,853,384 A * 12/1998 Bair ............................ 604/22
6,036,541 A *  3/2000 Koumatsu ................... 439/587
6,561,519 B1    5/2003 Frese et al.
6,843,480 B1 *  1/2005 Nelson et al. .............. 277/338

* cited by examiner

VENTED SEAL HAVING REDUNDANT SEALING COMPONENTS

BACKGROUND

Seals are typically used to prevent fluids from leaking or mixing. For example, a volume of fluid held at an elevated pressure can be isolated from a connected lower-pressure volume of fluid by a seal. Some conventional seals use one sealing component, such as an O-ring or gasket.

SUMMARY OF THE INVENTION

Although conventional seals are functional, they are not always satisfactory. For example, a leak from a higher-pressure fluid volume into the lower-pressure fluid volume may occur if the sealing component is defective, damaged, or worn out, if the sealing component has incorrect/incompatible dimensions, if debris becomes lodged between the seal and the sealing interface, or if insufficient lubrication (if needed) is used to aid sealing.

The inventor has discovered that many things may be done, individually or in combination, to increase the reliability of seals. For example, multiple or redundant sealing components can be used. If the fluid leaks past one seal, the next seal may stop it. Additionally, a vent can be located between the redundant sealing components. If fluid leaks past one seal, it will exit without applying any additional load on the subsequent seal(s). Also, the tolerance of the sealing component(s) can be improved to increase the amount of "squeeze" at the sealing interfaces and/or provide better, more consistent sealing engagement along the interfaces. Further still, offsetting sealing interfaces from each other can reduce the sensitivity of the sealing engagement to dimensional variations. By offsetting sealing interfaces, the engagement along one sealing interface is not affected by the engagement of an opposite sealing interface. This results in lower friction, less wear, and a longer life.

Some embodiments of the invention incorporate one or more aspects outlined above to increase reliability. For example, one embodiment is directed toward a seal having a ring-like body with a center, an inner axially extending surface, and an outer axially extending surface located radially around the center. A first projecting ring is integrally formed with the body and extends from the outer axial surface of the body in a radial direction away from the center of the body. A second projecting ring is integrally formed with the body and extends from the outer surface of the body in a radial direction away from the center of the body. The second projecting ring is axially disposed from the first projecting ring. A third projecting ring is integrally formed with the body and extends from the inner axial surface of the body in a radial direction toward the center of the body. A fourth projecting ring is integrally formed with the body and extends from the inner axial surface of the body in a radial direction toward the center of the body. The third projecting ring is axially disposed from the fourth projecting ring. Finally, an aperture extends between the inner and outer axially extending surfaces of the body. The aperture is located between the first and second projecting rings and between the third and fourth projecting rings.

Some embodiments are directed towards a seal including a generally cylindrically-shaped body having a center and several rings extending away from the body in a radial direction. A first and second ring extends from the body in a radial direction away from the center. The second ring is disposed axially from the first ring. A third ring and fourth ring extend from the body in a radial direction toward the center of the body. The third ring is disposed axially from the fourth ring and the third and fourth rings are axially offset with respect to the first and second rings. A vent extends through the body. The vent is located between the third and fourth rings and between the first and second rings.

Some embodiments are also directed to a seal adapted to provide a sealing engagement between a shaft and a passage surrounding the shaft. The seal has a body having at least one inner surface, at least one outer surface, and an aperture extending between the at least one inner surface and the at least one outer surface. A first and second band project from and are formed integral with the body. The first and second bands surround at least an axial portion of the outer surface of the body. Each is dimensioned to provide a sealing engagement with the passage. The first band is axially disposed from the second band and the aperture is located between the first and second band. A third and fourth band project from and are formed integral with the body. The third and fourth band surround at least an axial portion of the inner surface of the body and are dimensioned to provide a sealing engagement with the shaft. The third band is axially disposed from the fourth band and the aperture is located between the third and fourth band.

Some embodiments are also directed to a surgical cutting device including a housing having a first chamber, a second chamber, and a passage extending between the first and second chamber. A vent defined by a channel extends through the housing from the passage. A shaft extends at least partially through the housing. For example, a first end of the shaft is located in the first chamber and a second end of the shaft is located outside of the housing. The shaft extends from the first chamber at the first end and through the passage and the second chamber to the second end. A seal is located between the shaft and the passage to separate the first chamber from the second chamber. The seal includes a body having at least one inner surface positioned adjacent the shaft, at least one outer surface positioned adjacent the passage, and an aperture extending between the at least one inner surface and the at least one outer surface. A first and second band project from and are formed integral with the body. The first and second band each surround at least an axial portion of the outer surface of the body and are dimensioned to provide a sealing engagement with the passage. The first band is axially disposed from the second band and the aperture, wherein the aperture can be located between the first and second band. A third and fourth band project from and are formed integral with the body. The third and fourth band each surround at least an axial portion of the inner surface of the body and are dimensioned to provide a sealing engagement with the shaft. The third band is axially disposed from the fourth band and the aperture, wherein the aperture can be located between the third and fourth band.

Some embodiments are directed toward a method of sealing a gap between a shaft and a shaft housing. The method can include inserting a seal between the shaft and the shaft housing. The seal may have a body with at least one inner surface, at least one outer surface, and an aperture extending between the at least one inner surface and the at least one outer surface. A first and second band project from the body. The first and second band surround at least an axial portion of the outer surface of the body and are dimensioned to provide a sealing engagement with the shaft housing. The first band is axially disposed from the second band and the aperture is located between the first and second band. A third and fourth band project from the body. The third and fourth band surround at least an axial portion of the inner surface of the body and are dimensioned to provide a sealing engagement with the shaft. The third band is axially disposed from the fourth band and the aperture is located between the third and fourth band. The method can also include engaging the first and second band with the shaft housing and engaging the third and fourth band with the shaft. Finally, the method can include positioning the first band on a first side of a vent extending from the shaft housing and positioning the second band on a second side of the vent opposite the first side.

In some constructions of the above-described embodiments, the seal can be formed as a single unitary structure rather than comprising multiple parts. For example, the body of the seal and the sealing components can be integrally formed as a single structure through the use of relatively modern manufacturing techniques, such as injection molding or more specifically liquid rubber injection molding.

Further aspects of the invention, together with the organization and operation thereof, will become apparent from the following detailed description of the invention when taken in conjunction with the accompanying drawings.

BRIEF DESCRIPTION OF THE DRAWINGS

The invention is described with reference to the accompanying drawings. However, the drawings illustrate certain embodiments and examples only. The various elements and combinations of elements described below and illustrated in the drawings can be arranged and organized differently to result in embodiments which are still within the spirit and scope of the invention.

In the drawings, wherein like reference numerals indicate like parts.

DETAILED DESCRIPTION OF THE ILLUSTRATED EMBODIMENTS

Figure 1:
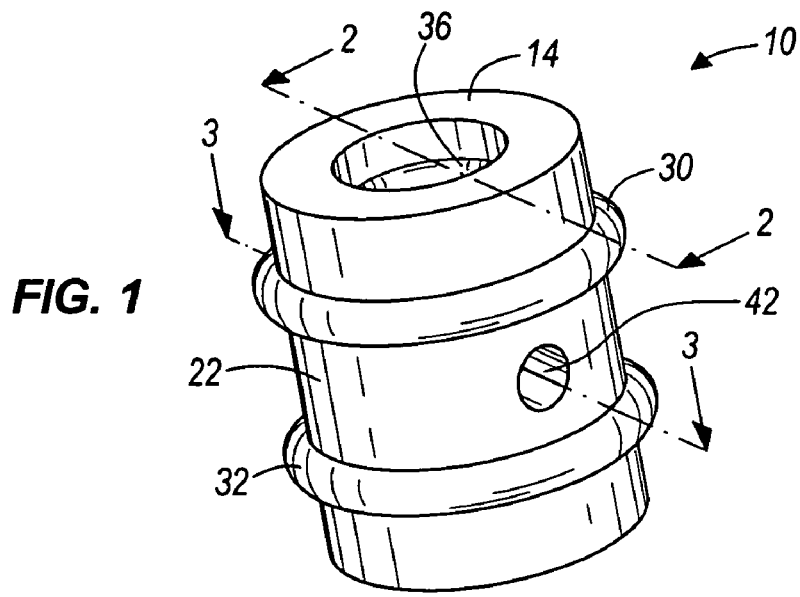
FIG. 1 is a perspective view of a seal embodying aspects of the invention.
Figure 2:
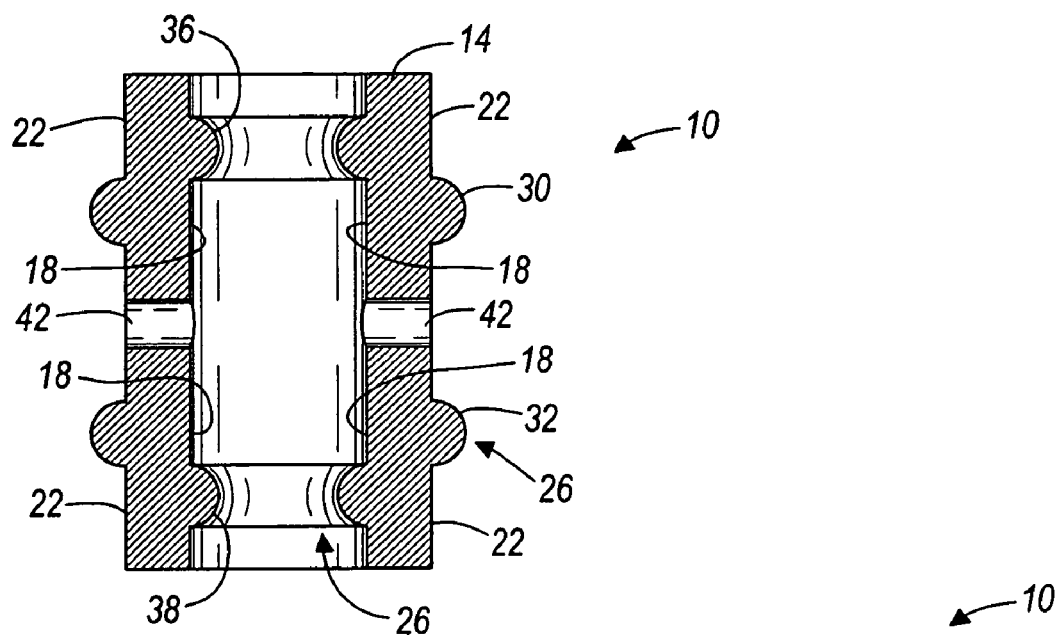
FIG. 2 is a side cross-sectional view taken along a longitudinal axis of the seal illustrated in FIG. 1.
Figure 3:
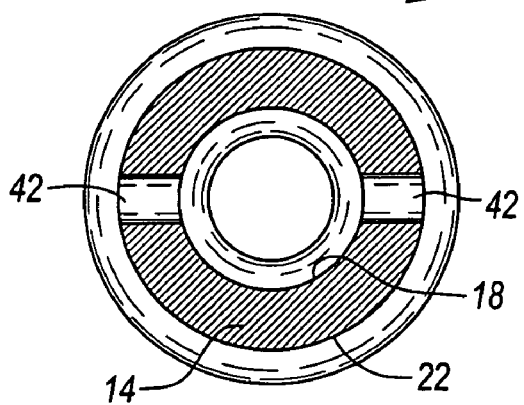
FIG. 3 is a top cross-sectional view taken perpendicular to the cross-sectional view of FIG. 2 of the seal illustrated in FIG. 1.

One embodiment of the seal 10 is illustrated in FIGS. 1–4. As illustrated, the seal 10 has a body 14 that is generally cylindrical. Although the body 14 of the illustrated embodiment is cylindrical, the body 14 and mating components can be of most any shape other than cylindrical. For example, the seal, body, and/or sealing components can be shaped like a polygon or any other shape desired to be sealed. Since the embodiment illustrated in FIGS. 1–4 has a cylindrical body 14, the body 14 appears to be ring-like from the top (FIG. 3).

In the embodiment shown, the body 14 has an inner surface 18 and an outer surface 22 that are located radially around a center of the body 14. The inner surface 18 is located radially inward with respect to the outer surface 22. As illustrated in FIG. 2, the inner and outer surfaces 18 and 22 both extend in a generally axial direction. Although the inner and outer axially extending surfaces 18 and 22 are illustrated as each having a constant radius, in other embodiments, the radius along these surfaces can vary. For example, the surface may provide smooth transitions between the body 14 and the sealing components 26.

As illustrated, a plurality of sealing components 26 are connected to the body 14. Specifically, four sealing components 26 are coupled to the body 14 along the inner and outer axially extending surfaces 18 and 22. Two of the sealing components are coupled to the inner axially extending surface 18 of the body 14 and two of the sealing components are coupled to the outer axially extending surface 22 of the body 14. Each set of sealing components provide redundant sealing engagement. In other embodiments, more sealing components can be used. Although the illustrated sealing components 26 are shown having a rounded cross-section, the sealing components can have a variety of shapes. For example, the sealing components can have a square cross-section, triangular cross-section, partially elliptical cross-section, and the like.

In some embodiments, the sealing components 26 are integrally formed with the body 14. For example, as illustrated in FIG. 2, first and second rings 30 and 32 are integrally formed with the body and extend or project from the outer axial surface of the body in a radial direction away from the center of the body. The second projecting ring 32 is axially disposed from the first projecting ring 30. Furthermore, third and fourth rings 36 and 38 are integrally formed with the body and extend or project from the inner axial surface of the body in a radial direction toward the center of the body. The third projecting ring 36 is axially disposed from the fourth projecting ring 38. The sealing components 26 can be integrally formed with the body 14 by using some relatively modern manufacturing techniques, such as injection molding.

Although the sealing components 26 of the illustrated embodiment are integrally formed with the body, in other embodiments, the sealing components 26 can be separate elements that are coupled to the body 14, such as O-rings. For example, a groove can be located around the body in positions corresponding to the illustrated position of the sealing components to provide a seat for the sealing components 26 to prevent them from moving relative to the body 14. In yet other embodiments, the sealing components 26 can be adhered or bonded to the body 14.

As illustrated in FIGS. 1–4, at least one aperture 42 can extend between the inner and outer axially extending surfaces 18 and 22 of the body 14. Specifically, the aperture 42 is located between the first and second projecting rings 30 and 32 and between the third and fourth projecting rings 36 and 38. This aperture 42 is generally considered to be a vent and preferably is located near a vent within the device being sealed (see FIG. 4). The seal vent 42 can prevent pressure from building up on one of the redundant sealing components within a set of redundant sealing components when the other sealing component within the set fails by venting leaked material through a channel in the device to the atmosphere or other holding chamber. As illustrated, some embodiments of the seal 10 can have more than one vent 42. However, some embodiments may only have one vent 42.

As best illustrated in FIG. 2, the first and second projecting rings 30 and 32 of this embodiment are equally spaced on either side of the aperture 42. Additionally, the third and fourth projecting rings 36 and 38 are equally spaced on either side of the aperture 42. In other embodiments, however, the sealing components 26 do not have to be equally spaced on either side of the aperture 42.

The inner and outer sealing components of the illustrated seal 10 are also offset from each other. Specifically, the first and second sealing components 30 and 32 are located a first axial distance from the aperture and the third and fourth sealing components 36 and 38 are located a second axial distance from the aperture. As illustrated, the second distance is greater than the first distance. In other embodiments, however, the first distance can be greater than the second distance. Alternatively, the inner and outer sealing interfaces can be aligned axially.

The seal 10 can be made of one or more materials. For example, some embodiments are made from an elastomer, while other embodiments are made from a soft polymer such as PTFE (Teflon). Furthermore, in some embodiments where the sealing components 26 are not integrally formed with the body 14, the sealing components 26 can be made from a first material and the body 14 can be made from a second material. The inner set of sealing components can also be made from a different material than the outer set of sealing components in some embodiments. In yet other embodiments, the sealing components 26 adjacent (or most likely to come into contact with) a first fluid can be one type of material, while the sealing components 26 adjacent (or most likely to come into contact with) a second fluid can be another type of material. These and other combinations of materials are possible.

Figure 4:
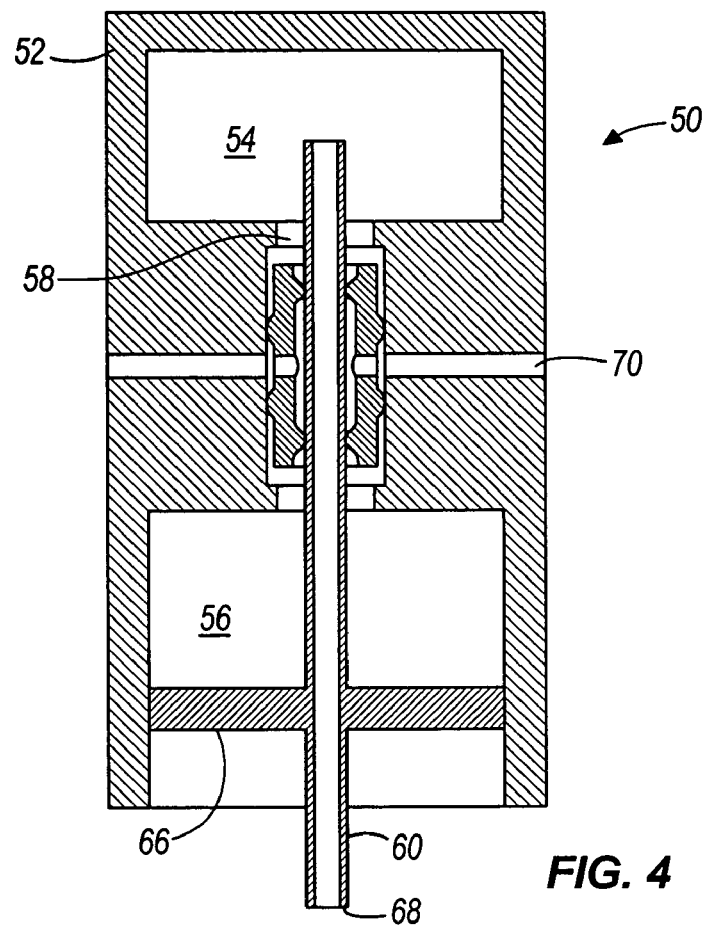
FIG. 4 is a side cross-sectional view of the seal illustrated in FIG. 1, wherein the seal is placed in an exemplary environment.

FIG. 4 illustrates one exemplary application of the seal 10. Specifically, the illustrated exemplary device 50 is a surgical cutter, such as a vitreous surgical cutter, for example. The device 50 has a housing 52 containing first and second chambers 54 and 56 connected by a passage 58. A shaft 60 extends from the first chamber 54 through the passage 58 and the second chamber 56. The shaft 60 of this embodiment is a hollow tube to allow the first chamber 54 to communicate with fluid in the eye for example. In other embodiments, however, the shaft 60 is not hollow. The first and second chambers 54 and 56 can contain different fluids (or a mix of fluids) and/or they can be maintained at different static or dynamic pressures. The seal 10 may be positioned between the two chambers to prevent the fluids within the chambers from mixing.

As illustrated in FIG. 4, the first and second projecting rings 30 and 32 of the seal 10 engage the passage's wall to provide a sealing engagement between the seal 10 and the housing 52. The third and fourth projecting rings 36 and 38 engage the outer surface of the shaft 60 to provide a sealing engagement between the seal 10 and the shaft 60. As discussed above, this embodiment of the seal 10 has offset sealing interfaces. This offsetting can help maintain proper sealing engagement of the interfaces despite dimensional variation in the size of the shaft 60, passage 58, body 14, or sealing components 26. Specifically, the sealing components 26 and the body 14 can be designed so that the radial width of the seal 10 is slightly larger than the largest acceptable width of the space between the passage wall 58 and the shaft 60 due to dimensional variation. If the width of the space between the passage wall 58 and the shaft 60 is less than the largest acceptable width, the offset sealing components 26 allow the body 14 to flex so the seal fits between the shaft 60 and the passage wall 58. Offsetting can provide a lower frictional engagement and a longer, more consistent life for the sealing components 26.

In the exemplary device illustrated in FIG. 4, the first chamber 54 contains Fluid B, which has a pressure that can vary over time or remain constant. Additionally, Fluid B can be near, below, or above ambient (in this embodiment, atmospheric) pressure. Fluid B could be any mixture of gasses, liquids, and solids. If Fluid B is below ambient pressure, a vacuum can be formed within this chamber. This vacuum can pull fluids and/or other materials through the hollow shaft 60.

The second chamber 56 contains Fluid A, which has a pressure that can vary over time, but is generally near or higher than ambient (in this embodiment, atmospheric) pressure. However, the pressure of Fluid A could remain constant and could be below ambient pressure. Fluid A could be any mixture of gasses, liquids, and solids.

The shaft 60 has a radially expanded portion 66 in the second chamber 56. The radially expanded portion 66 engages the radial walls of the second chamber 56. As the pressure changes on at least one side of the radially expanded portion 66, a force is applied to the radially expanded portion 66, which causes it to move axially. This causes the shaft to oscillate axially. Although an oscillating movement has just been described, the seal 10 would also work in a device that rotates, oscillates rotationally, or is stationary. Furthermore, the shaft 60 could be driven in other ways (e.g., electrically), rather than pneumatically.

As the shaft 60 oscillates, the tip 68 of the shaft can be used to "cut" by puncturing and removing small amounts of material at a relatively high rate of speed. As material is "cut," a vacuum in the first chamber can cause the cut material to be evacuated through the shaft 60 and into the first chamber 54.

As discussed above, the seal 10 may be placed in the passage between the two chambers 54, and 56 to prevent the fluids from mixing. If the outer sealing component 32 adjacent Fluid A fails, Fluid A may leak past it. As a safety measure, the outer sealing component 30 adjacent Fluid B will act redundantly to prevent leaked Fluid A from mixing with Fluid B. As another safety measure, a housing vent 70 will allow leaked Fluid A to vent out to ambient or some other controlled area. The vent 70 prevents additional pressure load on the non-failing seal component and reduces the chance that leaked fluid will leak past the non-failing component. However, if the inner sealing component 38 adjacent Fluid A fails, Fluid A could leak past by it, through aperture 42, and out the vent 70. A similar analysis applies to potential leaks with the sealing components adjacent Fluid B. Although FIG. 4 illustrates the vent 70 as being in communication with the ambient/atmosphere, some embodiments may provide another chamber in communication with the vent 70. Consequently, the vent 70 and tip 68 may not be at the same pressure.

The vent 70 on the housing can be designed to prevent fluid or materials from entering the passage 58 via the vent channel 70. For example, the vent channel can be provided with a one-way valve. Additionally, the channel can be tapered to discourage debris from entering the passage via the vent channel 70.

Figure 5:
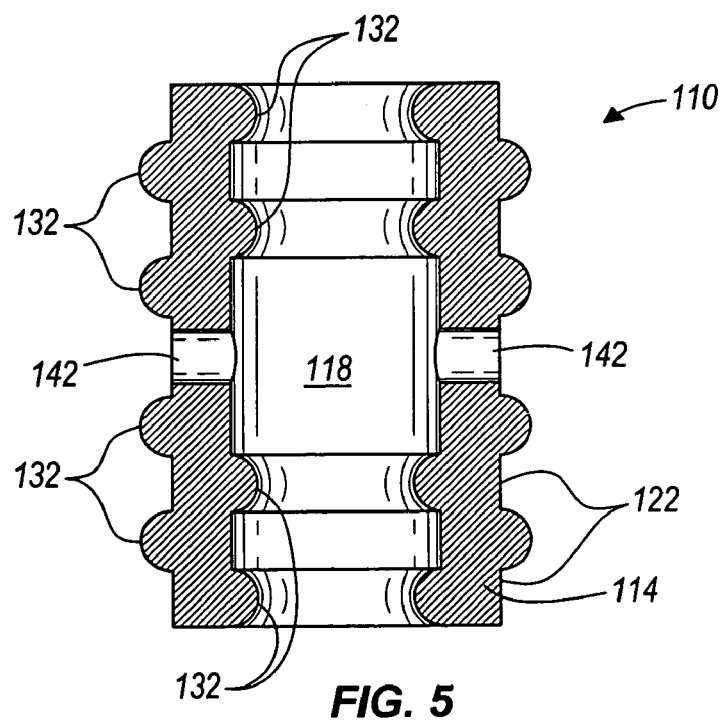
FIG. 5 is a side cross-sectional view of a seal embodying aspects of the invention.

FIG. 5 illustrates another exemplary embodiment of the seal. This exemplary embodiment has many similar aspects when compared with the embodiment in FIGS. 1–4. Specifically, each embodiment of the seal 10 and 110 has a body 14 and 114 having a plurality of sealing components 26 and 126 and at least one vent aperture 42 and 142 located between at least two sealing components. Since this embodiment has many similar features to the previous embodiment, generally only the differences between the embodiments will be discussed.

This embodiment of the seal 110 has more sealing components than the previous embodiment. As illustrated, the seal has redundant sealing components 126 on each side of the vent 142. Specifically, two sealing components 126 are located above (as illustrated) the vent 142 and below the vent 142 along each of the interior and exterior surfaces of the body 114. Although a total of four sealing components 126 are illustrated in FIG. 5, more or less sealing components can be used in other embodiments. Furthermore, the inner surface 118 of the seal 110 can have more or less sealing components than the outer surface 122.

Unlike the seal 10 of the FIG. 2, the body 114 of the seal 110 illustrated in FIG. 5 does not extend further than the sealing components at the axial extents of the body. Alternatively, the body 114 of the seal 110 can extend beyond the axial extents of the sealing components. Also, the seal 10 of FIG. 2 can be altered to eliminate the body 10 that extends beyond the axial extents of the sealing components 26.

The body 10 and 10 and the sealing components 26 and 126 of either illustrated seal 10 and 110 can have variety of shapes. For example, FIG. 3 and the discussion provided above clearly indicate that the seal can be circular or cylindrical. However, as mentioned above, the seal can also have a variety of shapes, such as triangular, square, rectangular, polygonal, or other shapes. For example, if the shaft of FIG. 4 were square, rather than circular in cross-section, it would be desirable to use a square seal. In that situation, the seal may be described with slightly different terminology. For example, the seal might be described as having a body with at least one inner surface, at least one outer surface, and an aperture extending between the at least one inner surface and the at least one outer surface. Furthermore, although it is not illustrated, a first and second band can project from and be formed integral with the body. The first and second band could surround at least an axial portion of the outer surface of the body and be dimensioned to provide a sealing engagement with the passage. The first band can be axially disposed from the second band and the aperture can be located between the first and second band. A third and fourth band can also project from and be formed integral with the body. The third and fourth band can surround at least an axial portion of the inner surface of the body and be dimensioned to provide a sealing engagement with the shaft. The third band can be axially disposed from the fourth band and the aperture can be located between the third and fourth band.

Other embodiments of the seal (not illustrated) can have an inner surface having a first cross-section and the outer surface having a second cross-section. For example, with reference to FIG. 4, the shaft 60 of this embodiment could be square, while the passage 58 could be generally circular. In such a circumstance, the inner sealing components would have a generally square cross-section (for a cross-section taken parallel to the cross-section of FIG. 3), while the outer sealing components would have a generally circular or ring-like cross-section. These and other alternative constructions can be formed using one or more relatively modern manufacturing techniques, such as injection molding.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. For example, various alternatives to the certain features and elements of the present invention are described with reference to specific embodiments of the present invention. With the exception of features, elements, and manners of operation that are mutually exclusive of or are inconsistent with each embodiment described above, it should be noted that the alternative features, elements, and manners of operation described with reference to one particular embodiment are applicable to the other embodiments.

We claim:
1. A surgical cutting device, comprising:
   a housing having a first chamber, a second chamber, and a passage extending between the first and second chamber;
   a vent defined by a channel extending through the housing from the passage;
   a shaft having a first end located in the first chamber and a second end located outside of the housing, the shaft extending from the first chamber at the first end and through the passage and the second chamber to the second end;
   a seal located between the shaft and the passage to separate the first chamber from the second chamber, the seal comprising:
   a body having at least one inner surface positioned adjacent the shaft, at least one outer surface positioned adjacent the passage, and an aperture extending between the at least one inner surface and the at least one outer surface,
   a first and second band projecting from and formed integral with the body, the first and second band each surrounding at least an axial portion of the outer surface of the body and dimensioned for sealing engagement with the passage, the first band axially disposed from the second band and the aperture; and
   a third and fourth band projecting from and formed integral with the body, the third and fourth band each surrounding at least an axial portion of the inner surface of the body and dimensioned for sealing engagement with the shaft, the third band axially disposed from the fourth band and the aperture.

2. The device of claim 1, wherein the third and fourth bands of the seal are axially offset with respect to the first and second bands of the seal.

3. The device of claim 1, wherein a first axial distance separates the third and fourth bands of the seal from each other and a second axial distance greater than the first axial distance separates the first and second bands of the seal from each other.

4. The device of claim 1, wherein the first and second bands of the seal are axially disposed from the aperture by substantially the same distance.

5. The device of claim 1, wherein the third and fourth bands of the seal are axially disposed from the aperture by substantially the same distance.

6. The device of claim 1, wherein the seal is made from an elastomer.

7. The device of claim 1, wherein the seal is made from a soft polymer.

8. The device of claim 1, wherein the shaft is configured to reciprocate within the passage to perform cutting operations.

9. The device of claim 8, wherein the shaft has a circular cross-section.

10. The device of claim 1, wherein the shaft is configured to rotate to perform cutting operations.

11. The device of claim 1, wherein the shaft is hollow and the first chamber is configured to have a pressure that is different than a pressure outside the housing and resulting in a pressure differential, the pressure differential capable of causing fluid to travel through the shaft.

12. The device of claim 1, wherein the aperture in the seal is in communication with the channel of the housing.

13. The device of claim 1, wherein the bands are formed integral with the body.

14. The device of claim 1, wherein a first axial distance separates the third and fourth bands of the seal from each other and a second axial distance less than the first axial distance separates the first and second bands of the seal from each other.

* * * * *

UNITED STATES PATENT AND TRADEMARK OFFICE
CERTIFICATE OF CORRECTION

PATENT NO. : 7,066,927 B2  Page 1 of 1
APPLICATION NO. : 10/758400
DATED : June 27, 2006
INVENTOR(S) : David Chen and Erik W. Peterson It is certified that error appears in the above-identified patent and that said Letters Patent is hereby corrected as shown below:

Column 7, line 14, delete the second number "10" and insert --110--.

Signed and Sealed this

Twelfth Day of September, 2006

JON W. DUDAS
*Director of the United States Patent and Trademark Office*